US009039700B2

(12) United States Patent
Kirschenman

(10) Patent No.: US 9,039,700 B2
(45) Date of Patent: May 26, 2015

(54) IRRIGATED ABLATION CATHETER WITH CONTACT FORCE SENSING MECHANISM

(75) Inventor: Mark B. Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 705 days.

(21) Appl. No.: 13/339,770

(22) Filed: Dec. 29, 2011

(65) Prior Publication Data

US 2013/0172784 A1      Jul. 4, 2013

(51) Int. Cl.
| A61B 5/00 | (2006.01) |
| A61B 18/14 | (2006.01) |
| A61B 18/00 | (2006.01) |
| A61B 19/00 | (2006.01) |

(52) U.S. Cl.
CPC ........... *A61B 18/1492* (2013.01); *A61B 5/6843* (2013.01); *A61B 5/6852* (2013.01); *A61B 2018/00029* (2013.01); *A61B 2018/00351* (2013.01); *A61B 2018/00839* (2013.01); *A61B 2018/1467* (2013.01); *A61B 2019/465* (2013.01); *A61B 2218/002* (2013.01)

(58) Field of Classification Search
CPC ............... A61B 5/6852; A61B 5/6843; A61B 2018/1467; A61B 2019/465; A61B 2018/00029; A61B 2018/00351; A61B 2018/00839; A61B 2218/002; A61B 18/1492
USPC ............................................ 606/41; 600/587
See application file for complete search history.

(56) References Cited

U.S. PATENT DOCUMENTS

| 3,911,199 | A * | 10/1975 | Fischer ........................... 174/42 |
| 5,695,473 | A * | 12/1997 | Olsen ............................ 604/153 |
| 6,002,972 | A * | 12/1999 | Palmer ............................... 701/4 |
| 6,167,763 | B1 * | 1/2001 | Tenerz et al. ................... 73/756 |
| 6,423,029 | B1 * | 7/2002 | Elsberry ......................... 604/65 |
| 2002/0123749 | A1 * | 9/2002 | Jain ................................. 606/41 |
| 2004/0034344 | A1 * | 2/2004 | Ryba ............................... 606/21 |
| 2005/0288657 | A1 * | 12/2005 | Lentz et al. ..................... 606/21 |
| 2006/0184165 | A1 * | 8/2006 | Webster et al. ................ 606/41 |
| 2007/0100332 | A1 * | 5/2007 | Paul et al. ....................... 606/41 |
| 2008/0161794 | A1 * | 7/2008 | Wang et al. ..................... 606/41 |
| 2008/0221508 | A1 * | 9/2008 | Abboud et al. ................ 604/30 |
| 2008/0294144 | A1 * | 11/2008 | Leo et al. ...................... 604/508 |
| 2009/0076476 | A1 * | 3/2009 | Barbagli et al. .............. 604/500 |

(Continued)

FOREIGN PATENT DOCUMENTS

WO    WO 2009/120982    10/2009

*Primary Examiner* — Carl H Layno
*Assistant Examiner* — Erin Piateski
(74) *Attorney, Agent, or Firm* — Dykema Gossett PLLC

(57) ABSTRACT

A catheter is configured to indicate contact force between the catheter and tissue. The catheter includes an elongate deformable shaft having proximal and distal ends. The catheter includes an inner tip member projecting outwardly from the distal end, the inner tip member defining a fluid delivery lumen extending therethrough, and an outer tip member coupled to the distal end and disposed about the inner tip member. The inner and outer tip members define a gap therebetween in fluid communication within the fluid delivery lumen and the tip members are configured such that the size of the gap varies in response to contact of the outer tip member with the tissue. The catheter further includes first and second fluid sensing tubes defining ports upstream and downstream from the gap; wherein a difference in fluid pressure between the ports is indicative a contact force between the catheter and the external surface.

20 Claims, 3 Drawing Sheets

(56) References Cited

U.S. PATENT DOCUMENTS

| | | |
|---|---|---|
| 2009/0177095 A1* | 7/2009 | Aeby et al. .................... 600/478 |
| 2009/0247942 A1 | 10/2009 | Kirschenman |
| 2009/0247944 A1 | 10/2009 | Kirschenman et al. |
| 2009/0247993 A1 | 10/2009 | Kirschenman et al. |
| 2009/0248042 A1 | 10/2009 | Kirschenman |
| 2010/0256558 A1 | 10/2010 | Olson et al. |
| 2011/0015569 A1 | 1/2011 | Kirschenman et al. |
| 2011/0162195 A1* | 7/2011 | Webster et al. .............. 29/592.1 |
| 2011/0270246 A1* | 11/2011 | Clark et al. .................... 606/41 |

* cited by examiner

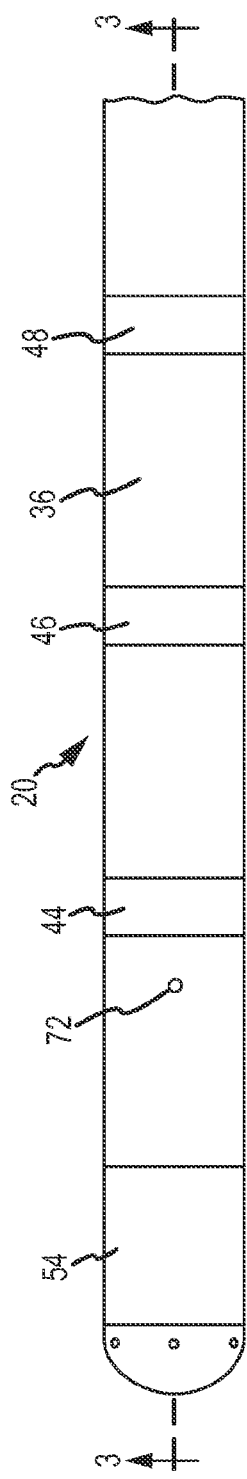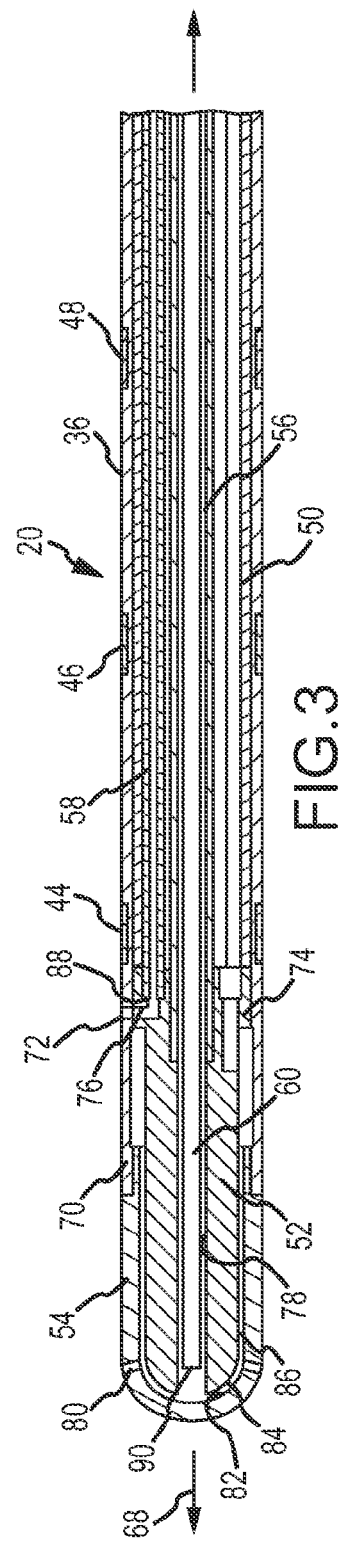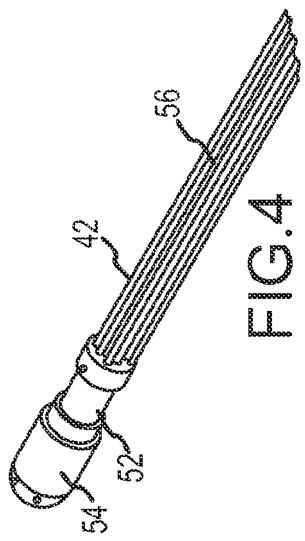

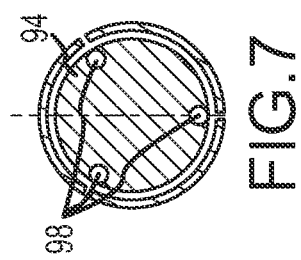
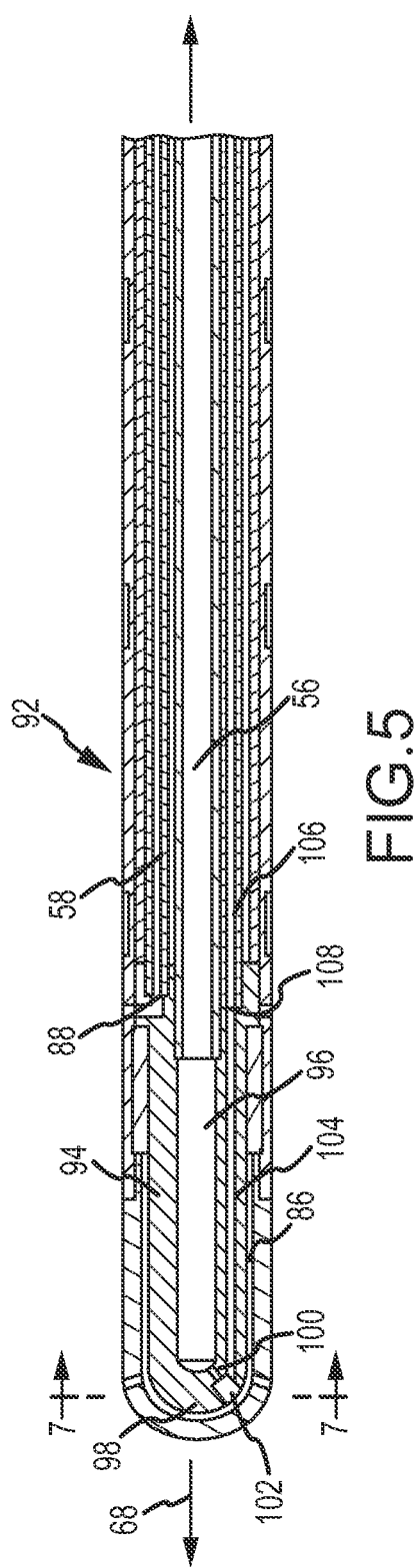
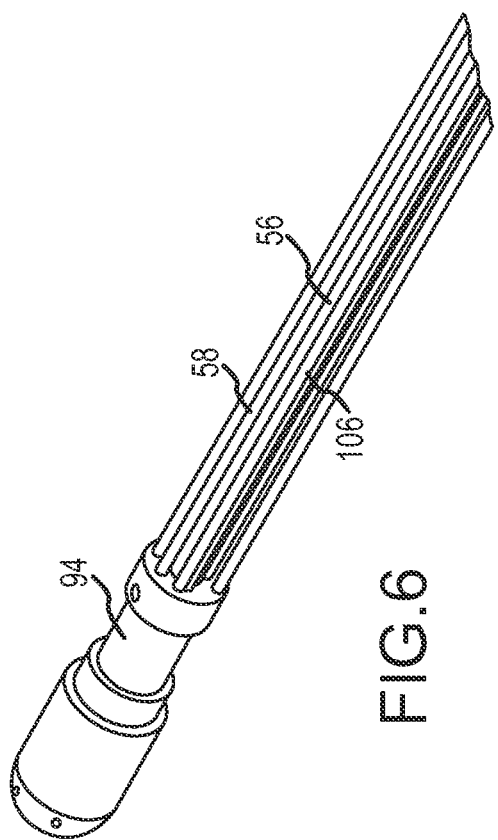

IRRIGATED ABLATION CATHETER WITH CONTACT FORCE SENSING MECHANISM

BACKGROUND OF THE INVENTION a. Field of the Invention

This invention relates to catheters. In particular, the instant invention relates to an irrigated ablation catheter configured to provide an indication of contact force between the catheter and tissue in a body.

b. Background Art

Catheters are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is inserted through the skin surface and a sheath having an inner diameter greater than the outer diameter of the catheter is threaded through the vasculature to a region of interest. The catheter is then moved longitudinally through the sheath to the region of interest either manually by a clinician or through the use of various types of robotic controls such as electromechanical drive systems.

Many conventional catheters include means for determining the degree of contact between the catheter and tissue and for controlling the catheter in response to the degree of contact. In the case of an electrophysiological mapping catheter, for example, sufficient contact is required to provide meaningful sensor outputs and accurate mapping of the heart. In the case of ablation catheters, sufficient contact is required for effective formation of ablative lesions in the tissue. A variety of mechanisms have been employed in catheters to determine contact force between catheters and tissue including, for example, strain gauges. Conventional mechanisms, however, are relatively complex and require additional components that increase the cost, size, and complexity of the catheter.

The inventor herein has recognized a need for a catheter that will minimize and/or eliminate one or more of the above-identified deficiencies.

BRIEF SUMMARY OF THE INVENTION

It is desirable to provide a catheter and a system for measuring contact force between the catheter and tissue in a body.

A catheter in accordance with one embodiment of the present invention includes an elongate deformable shaft having a proximal end and a distal end. The catheter further includes an inner tip member projecting outwardly from the distal end of the shaft. The inner tip member defines a fluid delivery lumen extending therethrough. The catheter further includes an outer tip member coupled to the distal end of the shaft and disposed about the inner tip member. An inner surface of the outer tip member and an outer surface of the inner tip member define a gap therebetween in fluid communication with, and configured to received fluid from, the fluid delivery lumen. The outer and inner tip members are configured such that a size of the gap varies in response to contact of the outer tip member with an external surface. The catheter further includes a first fluid sensing tube defining a first port upstream from the gap and a second fluid sensing tube defining a second port downstream from the gap. A difference in fluid pressure between the first and second ports is indicative of a contact force between the catheter and the external surface.

A system for measuring contact force between a catheter and tissue in a body in accordance with one embodiment of the present invention includes a catheter including an elongate deformable shaft having a proximal end and a distal end. The catheter further includes an inner tip member projecting outwardly from the distal end of the shaft. The inner tip member defines a fluid delivery lumen extending therethrough. The catheter further includes an outer tip member coupled to the distal end of the shaft and disposed about the inner tip member. An inner surface of the outer tip member and an outer surface of the inner tip member define a gap therebetween in fluid communication with, and configured to received fluid from, the fluid delivery lumen. The outer and inner tip members are configured such that a size of the gap varies in response to contact of the outer tip member with an external surface. The catheter further includes a first fluid sensing tube defining a first port upstream from the gap and a second fluid sensing tube defining a second port downstream from the gap. The system further includes a pressure sensor generating a signal indicative of a difference in fluid pressure between the first and second ports. The pressure sensor is configured to transmit the signal to an electronic control unit configured to determine a contact force between the catheter and the tissue responsive to the signal.

A catheter and system in accordance with the present invention are advantageous because the inventive catheter and system enable measurement of contact force between the catheter and tissue without the need for strain gauges or other types of conventional force sensors and associates wires or optic fibers. The inventive catheter and system therefore enable force measurements without substantially increasing the size, cost or complexity of the catheter.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 2 is a plan view of one embodiment of a catheter in accordance with the present teachings.

FIG. 3 is a cross-sectional view of the catheter of FIG. 2 taken along lines 3-3.

FIG. 4 is a perspective view of a portion of the catheter of FIG. 2.

FIG. 5 is a cross-sectional view of another embodiment of a catheter in accordance with the present teachings.

FIG. 6 is a perspective view of a portion of the catheter of FIG. 5.

FIG. 7 is a cross-sectional view of the catheter of FIG. 5 taken along lines 7-7.

DETAILED DESCRIPTION OF EMBODIMENTS OF THE INVENTION

Figure 1:
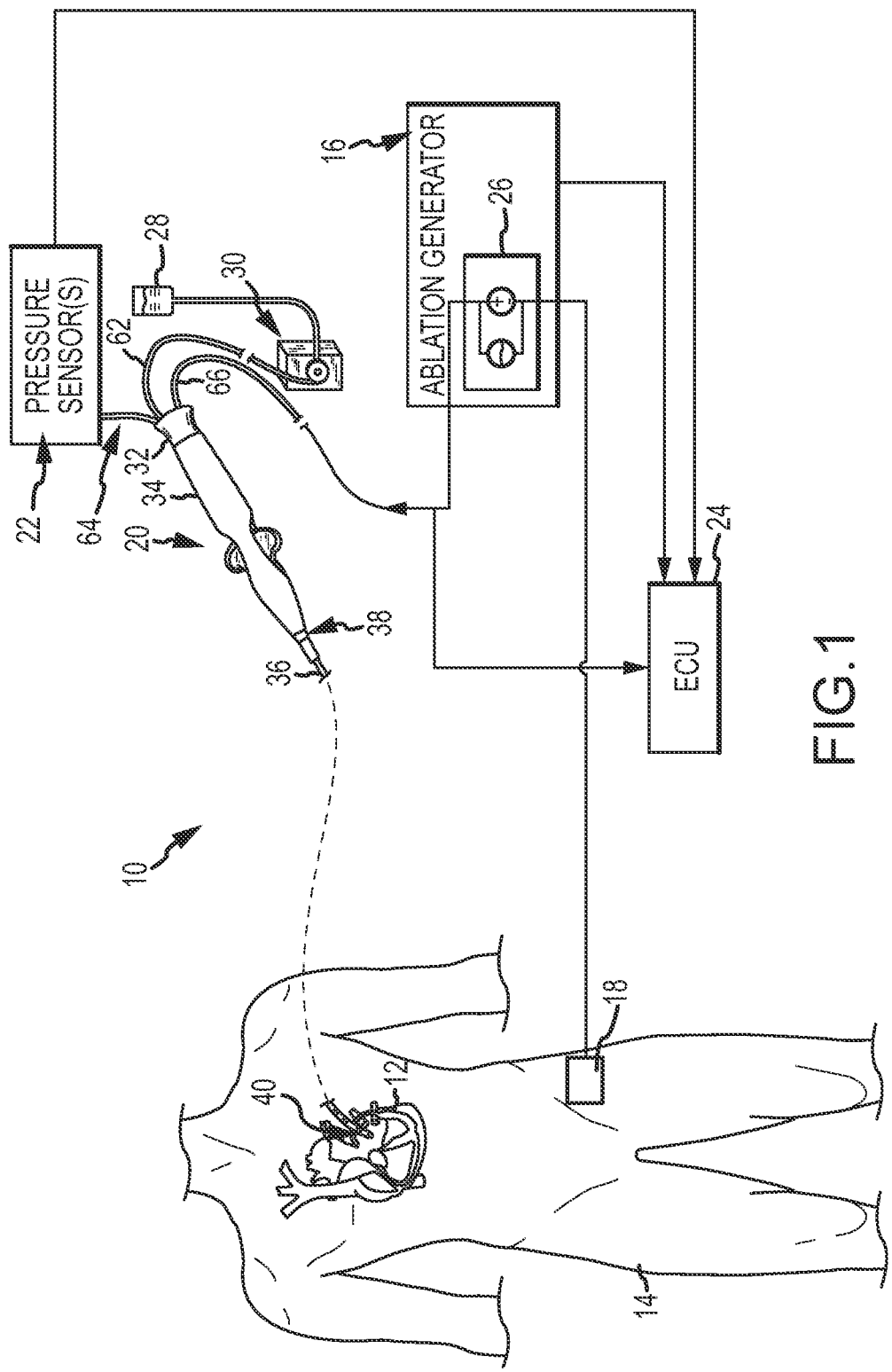
FIG. 1 is a diagrammatic view of a system for measuring contact force between a catheter and tissue in a body in accordance with one embodiment of the present teachings.

Referring now to the drawings wherein like reference numerals are used to identify identical components in the various views, FIG. 1 illustrates a system 10 for diagnosis and/or treatment of tissue 12 in a body 14. Although the illustrated system relates to diagnosis and treatment of cardiac tissues, it should be understood that the present invention may find application in the diagnosis and treatment of a variety of tissues. System 10 may include an ablation generator 16, a patch electrode 18, a catheter 20, one or more differential fluid pressure sensors 22, and an ECU 24.

Ablation generator 16 generates, delivers and controls RF energy used by catheter 20. Generator 16 is conventional in the art and may comprise the commercial unit available under the model number IBI-1500T RF Cardiac Ablation Generator, available from Irvine Biomedical, Inc., a St. Jude Medical Company. Generator 16 includes an RF ablation signal source 26 configured to generate an ablation signal that is output across a pair of source connectors: a positive polarity connector which may connect to an electrode on catheter 20; and a negative polarity connector which may be electrically connected by conductors or lead wires to one of patch electrodes 18. It should be understood that the term connectors as used herein does not imply a particular type of physical interface mechanism, but is rather broadly contemplated to represent one or more electrical nodes. Source 26 is configured to generate a signal at a predetermined frequency in accordance with one or more user specified parameters (e.g., power, time, etc.) and under the control of various feedback sensing and control circuitry as is know in the art. Source 26 may generate a signal, for example, with a frequency of about 450 kHz or greater. Generator 16 may also monitor various parameters associated with the ablation procedure including impedance, the temperature at the tip of catheter 20, ablation energy and the position of the catheter 20 and provide feedback to the clinician regarding these parameters.

Patch electrode 18 provides an RF or navigational signal injection path and/or is used to sense electrical potentials. Electrode 18 may also have additional purposes such as the generation of an electromechanical map or as part of a position sensing and navigation system for catheter 20 or other devices in body 14. Electrode 18 is made from flexible, electrically conductive material and is configured for affixation to body 14 such that electrode 18 is in electrical contact with the patient's skin. Electrode 18 may function as an RF indifferent/dispersive return for the RF ablation signal.

Catheter 20 may be used for examination, diagnosis and treatment of internal body tissues such as tissue 12. In accordance with one embodiment of the invention, catheter 20 comprises an ablation catheter and, more particularly, an irrigated radio-frequency (RF) ablation catheter. It should be understood, however, that the present invention can be implemented and practiced regardless of the type of ablation energy provided (e.g., cryoablation, ultrasound, etc.). Catheter 20 may be connected to a fluid source 28 having a biocompatible fluid such as saline through a pump 30 (which may comprise, for example, a fixed rate roller or peristaltic pump or variable volume syringe pump with a gravity feed supply from fluid source 28 as shown) for irrigation. Catheter 20 is also electrically connected to ablation generator 16 for delivery of RF energy. Catheter 20 may include a cable connector or interface 32, a handle 34, a shaft 36 having a proximal end 38 and a distal end 40 (as used herein, "proximal" refers to a direction toward the end of the catheter near the clinician, and "distal" refers to a direction away from the clinician and (generally) inside the body of a patient) and one or more diagnostic or treatment elements supported thereon. Referring briefly to FIGS. 2-4, in accordance with one embodiment of the invention, catheter 20 may further include a plurality of steering wires 42, proximal electrodes 44, 46, 48, a strut 50, an inner tip member 52, and outer tip member 54, a fluid delivery tube 56 and, fluid sensing tubes 58, 60. Catheter 20 may also include other conventional components not illustrated herein such as a temperature sensor, additional electrodes, one or more position sensors, and corresponding conductors or leads.

Referring again to FIG. 1, connector 32 may provide mechanical, fluid and electrical connection(s) for fluid conduits 62, 64 extending to and from pump 30 and pressure sensors 22, respectively, and cables 66 extending to and from ablation generator 16 and ECU 24. Connector 32 is conventional in the art and is disposed at a proximal end of catheter 20. Although the pressure sensor(s) 22 are illustrated as being positioned external to the catheter 20, in at least one embodiment, pressure sensor(s) 22 may be disposed within the catheter. For example, in one embodiment, pressure sensor(s) 22 may be housed within the catheter handle 34.

Handle 34 provides a location for the clinician to hold catheter 20 and may further provides means for steering or guiding shaft 36 within body 14. For example, handle 34 may include means to actuate various steering wires extending through catheter 20 to distal end 40 of shaft 36 to control translation and/or deflection of shaft 36. Handle 34 may also be conventional in the art and it will be understood that the construction of handle 34 may vary. It should be understood that catheter may be manipulated manually by a clinician using handle 34 or automatically through, for example, robotic controls. Exemplary robotic systems including such robotic controls may be found in one or more of the following: U.S. Published Patent Application No. 20090247942 published Oct. 1, 2009 and titled "Robotic Catheter Manipulator Assembly"; U.S. Published Patent Application No. 20090247944 published Oct. 1, 2009 and titled "Robotic Catheter Rotatable Device Cartridge"; U.S. Published Patent Application No. 20090247993 published Oct. 1, 2009 and titled "Robotic Catheter System"; U.S. Published Patent Application No. 20090248042 published Oct. 1, 2009 and titled "Model Catheter Input Device"; International Published Patent Application No. WO 2009/120982 published Oct. 1, 2009 and titled "Robotic Catheter System With Dynamic Response"; U.S. Published Patent Application No. 20100256558 published Oct. 7, 2011 and titled "Robotic Catheter System"; and U.S. Published Patent Application No. 2011/0015569 published Jan. 20, 2011 and titled "Robotic Catheter System Input Device", the entire disclosures of which are incorporated herein by reference.

Referring again to FIGS. 2-3, shaft 36 provides structural support to the other components of catheter 20 and may also permit transport, delivery and/or removal of fluids (including irrigation fluids and bodily fluids), medicines, and/or surgical tools or instruments to and from tissue 12. Shaft 36 is an elongate, tubular, flexible/deformable member configured for movement within body 14 (FIG. 1) and has a central axis 68. Shaft 36 may be introduced into a blood vessel or other structure within body 14 through a conventional introducer. Shaft 36 may then be steered or guided through body 14 to a desired location such as tissue 12 with a guiding introducer such as the Agilis™ NxT steerable introducer available from St. Jude Medical, Inc. or with guide wires or other means known in the art. Shaft 36 may be made from a conventional polymeric materials such as polyurethane, polyfluoroethylene (PTFE) including PTFE sold under the registered trademark "TEFLON" by E.I. DuPont de Nemours & Co. Corp., polyether block amides, and nylon or thermoplastic elastomers such as the elastomer sold under the registered trademark "PEBAX" by Arkema, Inc. At least a section 70 located at the distal end 40 (FIG. 1) of shaft 36 is made from an elastomeric material for a purpose described hereinbelow. Shaft 36 supports pull wires 42, proximal electrodes 44, 46, 48, strut 50, outer tip member 54, fluid delivery tube 56, sensing tubes 58, 60 and associated conductors, and possibly additional electronics used for signal processing or conditioning. Shaft 36 further defines one or more lumens configured to house and/or transport pull wires 42, strut 50, fluid delivery and sensing tubes 56, 58, 60, and associated electrical conductors, fluids or surgical tools. Referring to FIG. 2, shaft 36 defines a port 72 in a radially outer surface distal to electrode 44 for a purpose described hereinbelow.

Steering wires 42 control deflection of catheter 20. Wires 42 are conventional in the art and extend through shaft for connection to a proximal end of inner tip member 52. Using handle 34 or robotic controls disposed at a proximal end of catheter 20, a clinician applies tension to one or more of wires 42 to control deflection of the distal end 40 of catheter 20. In the illustrated embodiment, catheter 20 includes four steering wires 42 such that tension on individual wires results in a downward pull, upward pull, leftward pull and rightward pull of the distal end 40 of catheter 20. In at least one embodiment, tension may be applied to multiple pull wires at or about the same time to effectuate movement in-between two of the aforementioned directions.

Electrodes 44, 46, 48 may be provided for a variety of diagnostic and therapeutic purposes including, for example, electrophysiological studies, catheter identification and location, pacing, cardiac mapping and ablation. Electrodes 44, 46, 48 may be made from conventional conductive metals such as platinum, iridium, gold, and silver and metal alloys including stainless steel and Nitinol. Electrodes 44, 46, 48 are supported on an radially outer surface of shaft 36 and comprise ring electrodes in the illustrated embodiment. It should be understood, however, that the number, orientation and purpose of electrodes 44, 46, 48 may vary.

Strut 50 provides support to inner tip member 52 to position and orient tip member 52 in a predetermined manner relative to the other components of catheter 20. Strut 52 is disposed within shaft 36 and may be centered along axis 68. Strut 50 may be tubular and define a lumen through which fluid delivery tube 56 and fluid sensing tubes 58, 60, among other components, may extend. Strut 50 made be made from conventional polymers including those used for shaft 36 of catheter 20 and may included a braided layer or comprise a tube that is laser cut into a supporting structure. Strut 50 is flexible, but resists compression along axis 68. Strut 50 may be coupled to tip member 52 through adhesive bonding or in other ways customary in the art.

Inner tip member 52 is configured to deliver fluid to a gap 86 between inner and outer tip members 52, 54. Inner tip member 52 also provides a means for transmitting movements of steering wires 42 to deflection of the distal end 40 of catheter 20. Member 52 is supported within shaft 36 by strut 50 and projects outwardly from the distal end of shaft 36. Member 52 is located distally of steering wires 42 and electrodes 44, 46, 48. Member 52 is generally annular in shape with a spherical tip at a distal end. A proximal end of member 52 defines an enlarged diameter section 74 having an outer diameter about equal to an inner diameter of shaft 36. Section 74 is connected to steering wires 42 and functions similar to a conventional pull ring to translate tension on one or more of the steering wires 42 into deflection of catheter 20 within body 14. Tip member 52 defines a lumen 76 extending from a proximal end of member 52 to port 72 on shaft 36. The diameter of lumen 76 varies to define a shoulder against which a distal end of fluid sensing tube 58 is engaged. Tip member 52 also defines a fluid delivery lumen 78 extending therethrough from a proximal end of member 52 to a distal end of member 52 and centered about axis 68. The diameter of lumen 78 also varies to define a shoulder against which a distal end of fluid delivery tube 56 is engaged.

Outer tip member 54 may function as an electrode for diagnostic purposes and/or to deliver ablation energy to tissue 12. Member 54 may be made from conventional conductive metals such as platinum, iridium, gold, and silver and metal alloys including stainless steel and Nitinol. Member 54 is generally annular in cross-section and defines a spherical tip at a distal end for atraumatic engagement with tissue 12. Member 54 defines a plurality of ports 80 through which irrigating fluid may flow to prevent or reduce thrombogenic events and/or to provide tissue/electrode cooling during ablation. Member 54 is coupled to distal end section 70 of shaft 36 distally of steering wires 42 and electrodes 44, 46, 48. An inner surface 82 of member 54 is spaced from an outer surface 84 of inner tip member 52 to define a gap 86 therebetween. Gap 86 is in fluid communication with fluid delivery lumen 78 in member 52 and irrigation ports 80 in member 54 and is configured to received fluid from lumen 78 and deliver fluid to ports 80. In the absence of an external force, fluid flow from lumen 78 and the elastomeric nature of section 70 of shaft 36 help to maintain a relatively constant distance between surfaces 82, 84 of members 54, 52 and a relative constant size of gap 86. Engagement between member 54 and an external surface such as tissue 12, however, may cause outer tip member 54 to move relative to inner time member 52 by virtue of the contact force between tip member 54 and tissue 12 and the compression of section 70 of shaft 36 thereby causing variation in the distance between surfaces 82, 84 of members 54, 52, and the shape and/or size of gap 86. The change in gap 86 increases resistance to fluid flow and back pressure. The fluid pressure between surfaces 82, 84 of members 54, 52 acts as a spring exerting a biasing force in opposition to the contact force, effectively providing a variable distance that can be measured and is indicative of contact force between catheter 20 and tissue 12.

Fluid delivery tube 56 is provided to transport irrigation fluid from fluid source 28 to lumen 78 in inner tip member 52. Tube 56 may be made from conventional polymers and may extend from connector 32 in handle 34 through shaft 36 to lumen 78 in tip member 52. Tube 56 may be centered within shaft 36 along axis 68.

Fluid sensing tubes 58, 60 are provided to allow measurement of a differential fluid pressure on either side of gap 86. Sensing tubes 58, 60 may again be made from conventional polymers. Sensing tube 58 is in fluid communication with lumen 76 in inner tip member 52 and defines a port 88 at a distal end that is downstream from gap 86 and in fluid communication with lumen 76 and port 72 in shaft 36, and thus, with a region external to catheter 20. Sensing tube 60 is in fluid communication with lumen 78 in inner tip member 52 and defines a port 90 at a distal end that is upstream from gap 86 and preferably close to gap 86. In accordance with one embodiment of the invention, sensing tube 60 may be concentric with delivery tube 56 to conserve space. In particular, sensing tube 60 may be disposed within and surrounded by fluid delivery tube 56.

Referring again to FIG. 1, pressure sensor 22 generates a signal indicative of a difference in fluid pressure between ports 88, 90 of sensing tubes 58, 60 (FIG. 3). Sensor 22 may comprise a conventional differential fluid pressure sensor. Because sensor 22 determines a pressure differential between ports 88, 90, sensor 22 allows determination of changes in fluid pressure in gap 68 regardless of flow rates.

Referring still to FIG. 1, electronic control unit (ECU) 24 may provide a means for determining a contact force between catheter 20 and tissue 12 responsive to the signal generated by pressure sensor 22. ECU 24 may comprise a programmable microprocessor or microcontroller or may comprise an application specific integrated circuit (ASIC). ECU 24 may include a central processing unit (CPU) and an input/output (I/O) interface through which ECU 24 may receive a plurality of input signals including signals generated by generator 16, electrode 18, catheter 20 and pressure sensor 22 and generate a plurality of output signals including those used to control and/or provide data to generator 16, catheter 20 and input/output devices such as displays or haptic-feedback systems used by the clinician. ECU 24 may translate the fluid pressure measured by sensor 22 directly into an output value or may process the measurement by, for example correlating the measured pressure to fluid delivery flow rates to improve accuracy.

Referring now to FIGS. 5-7, a catheter 92 in accordance with another embodiment of the present invention is illustrated. Catheter 92 is substantially similar to catheter 20 and discussion to common components may be referenced hereinabove. Catheter 92 differs from catheter 20 in that catheter 92 is modified to create a plurality of pressure measurement locations upstream of gap 68. By obtaining pressure measurements at different locations relative to gap 68 ECU 24 is able to determine not only the magnitude of contact force resulting from engagement of catheter 20 and tissue 12, but also the direction of that force.

Catheter 92 includes an inner tip member 94 that is substantially similar to tip member 52 of catheter 20 discussed hereinabove. Tip member 94 differs from tip member 52 in that tip member 94 includes a fluid delivery lumen 96 that splits into a plurality of branch lumens 98 at a distal end. Referring to FIG. 7, in the illustrated embodiment, fluid delivery lumen 96 splits into three branch lumens 98 in fluid communication with gap 86. Branch lumens 98 may be equally circumferentially spaced about axis 68. Referring again to FIG. 5, the diameter of each branch lumen 98 varies with a reduced diameter section 100 branching from the main body of lumen 96 and an increased diameter section 102 adjacent gap 86. The variation in diameter enables each branch lumen 98 to act as metering orifice to enable independent sensing of flow while being fed from a common source in delivery tube 56. Inner tip member 94 further defines fluid sensing lumens 104 in communication with each branch lumen 98. Sensing lumens 104 may terminate in increased diameter sections 102 of corresponding branch lumens 98.

Catheter 92 also employs a plurality of fluid sensing tubes 106 in fluid communication with fluid sensing lumens 104 of tip member 94 and defining ports 108 in different locations upstream from gap 86. In the illustrated embodiment, catheter 92 employs three fluid sensing tubes 106 terminating in ports 108 that are equally circumferentially spaced about axis 68. It should be understood, however that the number of tubes 106 and the arrangement of ports 108 may vary depending on the degree of resolution desired. Individual differential pressure sensors 22 may generate signals indicative of a difference in fluid pressure between port 88 of sensing tube 58 and a port 108 of a corresponding sensing tube 106, for example. Using a plurality of differential pressure measurements generated by the sensors 22, ECU 24 can determine the magnitude of the contact force between catheter 92 and tissue 12 (FIG. 1) and the direction of that force.

A catheter and system in accordance with the present invention are advantageous because the inventive catheter and system enable measurement of contact force between the catheter and tissue without the need for strain gauges or other types of conventional force sensors and associates wires or optic fibers. The inventive catheter and system therefore enable force measurements without substantially increasing the size, cost or complexity of the catheter.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

Although the various embodiments of the devices have been described herein in connection with certain disclosed embodiments, many modifications and variations to those embodiments may be implemented. For example, particular features, structures, or characteristics described above may be combined in any suitable manner in one or more embodiments. Thus, the particular features, structures, or characteristics illustrated or described in connection with one embodiment may be combined, in whole or in part, with the features structures, or characteristics of one or more other embodiments without limitation unless illogical or non-functional. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising:
   an elongate deformable shaft having a proximal end and a distal end;
   an inner tip member projecting outwardly from said distal end of said shaft, said inner tip member defining a fluid delivery lumen extending therethrough;
   an outer tip member coupled to said distal end of said shaft and disposed about said inner tip member, an inner surface of said outer tip member and an outer surface of said inner tip member defining a gap therebetween in fluid communication with, and
   configured to receive fluid from said fluid delivery lumen, wherein said outer and inner tip members are configured such that a size of said gap varies in response to contact of said outer tip member with an external surface;

a first fluid sensing tube defining a first port upstream from said gap; and, a second fluid sensing tube defining a second port downstream from said gap;

wherein a pressure sensor disposed in the catheter handle or outside the catheter is configured to measure the difference in fluid pressure between the first and second ports;

and wherein said difference in fluid pressure between said first and second ports is indicative of a contact force between said catheter and said external surface.

2. The catheter of claim 1 further comprising a strut disposed within said shaft, said inner tip member supported on said strut.

3. The catheter of claim 1 wherein said fluid delivery lumen is disposed along a center axis of said inner tip member.

4. The catheter of claim 1 wherein said first fluid sensing tube is concentric with said fluid delivery lumen.

5. The catheter of claim 1 wherein said fluid delivery lumen surrounds said first fluid sensing tube.

6. The catheter of claim 1 wherein said outer tip member comprises an electrode.

7. The catheter of claim 6 wherein said electrode is configured to deliver ablation energy to said external surface.

8. The catheter of claim 1 wherein said second port is in fluid communication with a region outside said shaft.

9. The catheter of claim 1 further comprising a third fluid sensing tube defining a third port upstream from said gap wherein a difference in fluid pressure between said second and third ports is indicative of a contact force between said catheter and said external surface.

10. The catheter of claim 9 further comprising a fourth fluid sensing tube defining a fourth port upstream from said gap wherein a difference in fluid pressure between said second and fourth ports is indicative of a contact force between said catheter and said external surface.

11. The catheter of claim 1 wherein said distal end of said shaft comprises an elastomeric material configured such that contact of said outer tip member with said external surface causes compression of said distal end of said shaft and variation in said size of said gap.

12. The catheter of claim 1 wherein said outer and inner tip members are configured such that when fluid is flowing through said gap, fluid pressure between said inner surface of said outer tip member and said outer surface of said inner tip member acts as a spring exerting a biasing force in opposition to said contact force.

13. A system for measuring contact force between a catheter and tissue in a body, the system comprising:

a catheter, comprising:

an elongate deformable shaft having a proximal end and a distal end;

an inner tip member projecting outwardly from the distal end of said shaft, said inner tip member defining a fluid delivery lumen extending therethrough;

an outer tip member coupled to said distal end of said shaft and disposed about said inner tip member, an inner surface of said outer tip member and an outer surface of said inner tip member defining a gap therebetween in fluid communication with, and configured to receive fluid from, said fluid delivery lumen, wherein said outer and inner tip members are configured such that a size of said gap varies in response to contact of said outer tip member with an external surface;

a first fluid sensing tube defining a first port upstream from said gap; and, a second fluid sensing tube defining a second port downstream from said gap; and, a pressure sensor disposed in the catheter handle or outside the catheter, configured to (i) measure a difference in fluid pressure between said first and second ports and (ii) generate a signal indicative of said difference in fluid pressure between said first and second ports;

wherein said pressure sensor is configured to transmit said signal to an electronic control unit configured to determine a contact force between said catheter and said tissue responsive to said signal.

14. The system of claim 13 wherein said fluid delivery lumen surrounds said first fluid sensing tube.

15. The system of claim 13 wherein said outer tip member comprises an electrode.

16. The system of claim 13 wherein said second port is in fluid communication with a region outside said shaft.

17. The system of claim 13 further comprising a third fluid sensing tube defining a third port upstream from said gap wherein a difference in fluid pressure between said second and third ports is indicative of a contact force between said catheter and said external surface.

18. The system of claim 17 further comprising a fourth fluid sensing tube defining a fourth port upstream from said gap wherein a difference in fluid pressure between said second and fourth ports is indicative of a contact force between said catheter and said external surface.

19. The system of claim 13 wherein said distal end of said shaft comprises an elastomeric material configured such that contact of said outer tip member with said external surface causes compression of said distal end of said shaft and variation in said size of said gap.

20. The system of claim 13 wherein said outer and inner tip members are configured such that when fluid is flowing through said gap, fluid pressure between said inner surface of said outer tip member and said outer surface of said inner tip member acts as a spring exerting a biasing force in opposition to said contact force.

* * * * *